United States Patent [19]
Webster

[11] 4,183,552
[45] Jan. 15, 1980

[54] APPARATUS AND METHOD FOR RECORDING THE WALKING ABILITY OF AN INDIVIDUAL

[76] Inventor: David F. Webster, 1325A Edwards Ave., Santa Rosa, Calif. 95401

[21] Appl. No.: 862,093

[22] Filed: Dec. 19, 1977

Related U.S. Application Data

[63] Continuation-in-part of Ser. No. 773,683, Mar. 22, 1977, abandoned.

[51] Int. Cl.² .............................................. B41L 1/00
[52] U.S. Cl. ................................... 282/1 B; 35/29 R; 346/135.1
[58] Field of Search ....................... 35/29 R; 273/1 R; 282/1 B, 11.5 A, 11.5 R; 283/1 A; 346/135

[56] References Cited

U.S. PATENT DOCUMENTS

| | | | |
|---|---|---|---|
| 233,482 | 10/1880 | DeLong | 283/1 A |
| 1,225,500 | 5/1917 | Rosino | 282/3 R |
| 1,331,823 | 2/1920 | Phillips | 282/1 B |
| 1,543,747 | 6/1925 | Brey | 282/1 B |
| 2,998,983 | 9/1961 | Digate | 282/1 B |
| 3,016,812 | 1/1962 | Chatlain | 35/29 F UX |
| 3,223,437 | 12/1965 | Bertsch | 282/11.5 A |
| 3,419,286 | 12/1968 | Noonan | 282/11.5 A |
| 3,545,747 | 12/1970 | Thomas | 273/1 R |

OTHER PUBLICATIONS

"Ski Aid" Parade Section of Washington Post, p. 19, Mar. 12, 1967.
"All-Purpose Broad/Long Jump Mat", p. 15 of Cleo Catalog prior to Feb. 28, 1976.

Primary Examiner—Harland S. Skogquist
Attorney, Agent, or Firm—Eckhoff, Hoppe, Slick, Mitchell & Anderson

[57] ABSTRACT

A simple form of testing device is provided to record an individual's walking ability under the conditions existing at the time of the test. The individual's walking ability may be open to question because of ill health occasioned by a stroke or because of a suspicion that the individual is under the influence of alcohol or a drug.

13 Claims, 26 Drawing Figures

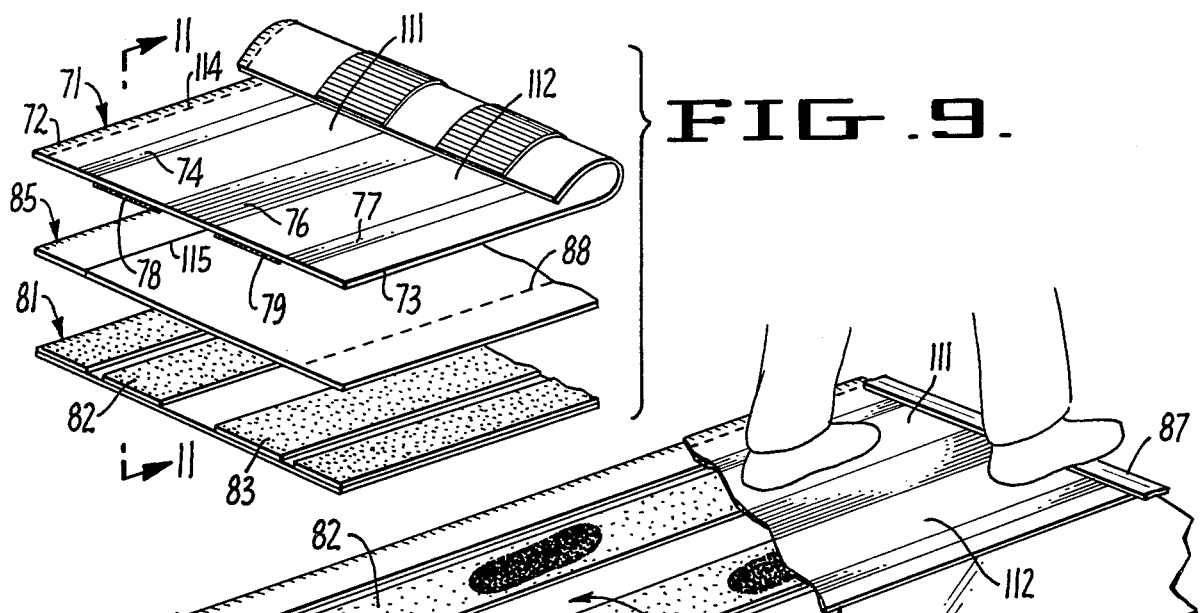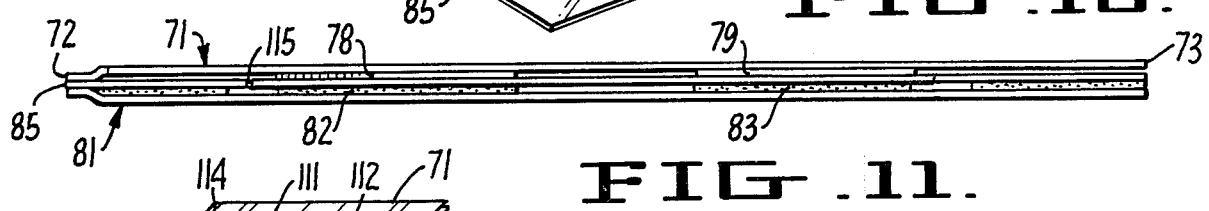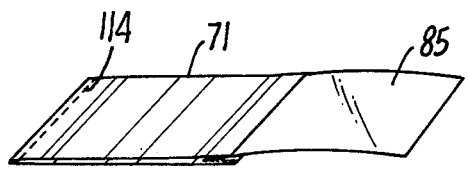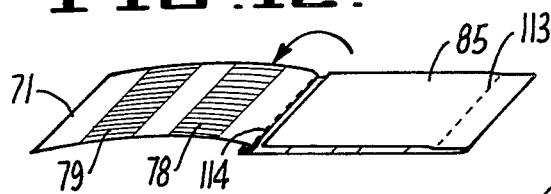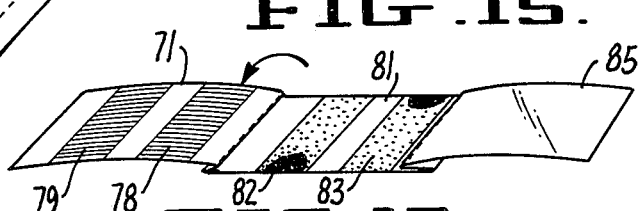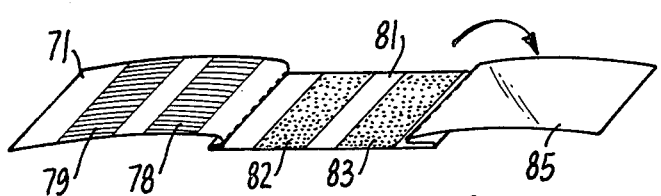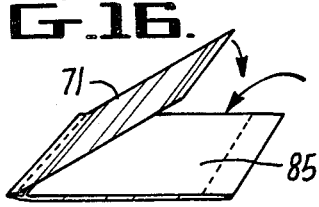

APPARATUS AND METHOD FOR RECORDING THE WALKING ABILITY OF AN INDIVIDUAL

BACKGROUND OF THE INVENTION

This application is a continuation-in-part of application Ser. No. 773,683, filed Mar. 22, 1977 now abandoned.

The test device and the method of the present invention provide a permanent and irrefutable record of the individual's walking ability as of the time of the test.

SUMMARY OF THE INVENTION

It is in general the broad object of the present invention to provide a simple test device which, when correctly utilized in accordance with the method of this invention, provides a permanent and irrefutable record of the individual's ability to walk a straight line. The footprints of the individual are recorded as a written record which can be suitably exhibited at any later time.

The method and device are based on the broad use of what can be characterized as an endless blank form. These are readily manufactured in a well-known manner. I modify these, however, incorporating a suitable inking element and a print receiving element upon which a footprint is applied when the pressure of a foot is placed upon the inking element to leave a permanent record of just where the foot was placed.

BRIEF DESCRIPTION OF THE DRAWINGS

FIG. 9 is an exploded view showing in a superimposed relationship the several elements making up another form of the test device of the present invention.

FIG. 10 is a perspective view showing the test device of FIG. 9 in use.

FIG. 11 is a section taken along the line 11—11 in FIG. 9.

FIG. 12 is a perspective view of the device in assembled form.

FIGS. 13 through 17 illustrate successive steps in the preparation of the device for use, in use, and following use, with the device assembled after the record has been made.

DESCRIPTION OF THE PREFERRED EMBODIMENT

Figure 3:
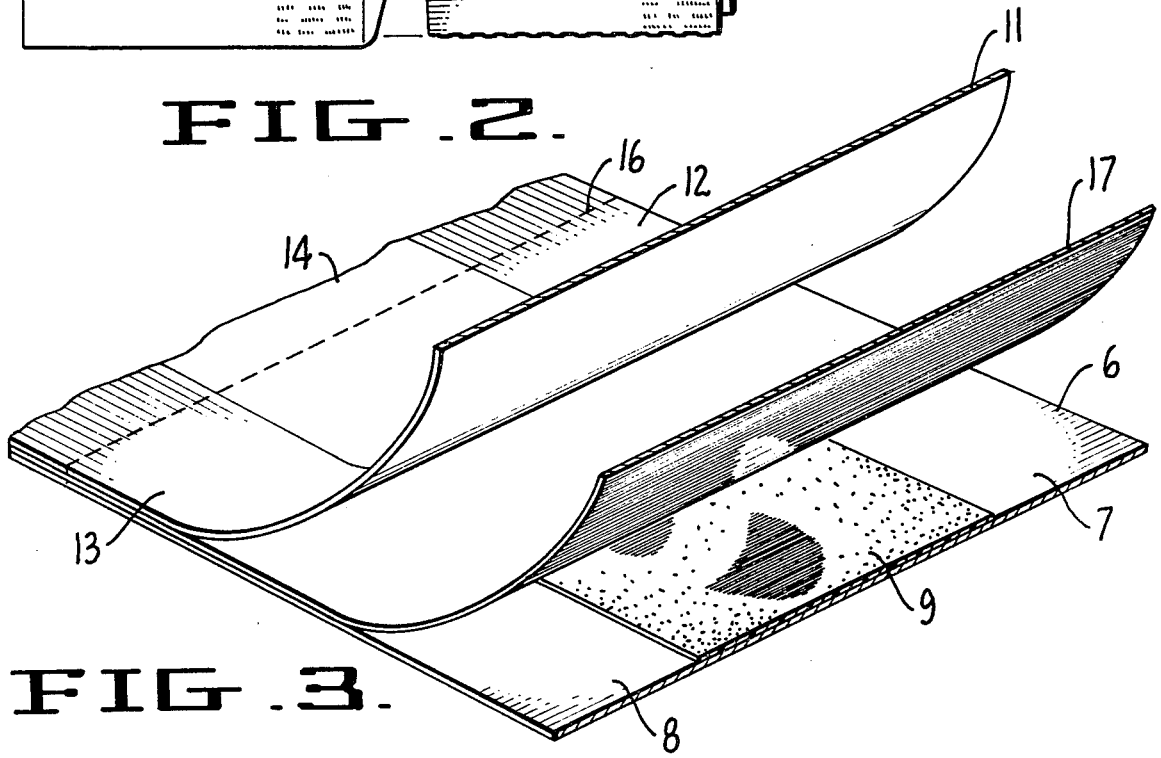
FIG. 3 is another perspective view showing a cross section through the test device.

Referring to the drawings and particularly to FIG. 3, the test device comprises a base sheet 6 having opposite marginal edges 7 and 8 on either side of a central portion 9.

An overlay sheet 11 is provided as the upper or topmost layer. The longitudinal edges 12 and 13 are printed in a distinctive color such as orange or red to provide an intermediate or central portion 14 which is white and provides a longitudinally extending white line. Normally the structure is made up in a plurality of sections, and in FIGS. 1 and 2 I have shown the several sections joined together along the outer edges and having fold lines 16.

Intermediate the uppermost layer 11 and the lowermost layer 6, I provide a sheet of carbon paper 17 or a layer of a non-drying ink. When carbon paper is used, a strip coating of light adhesive is laid on the lower sheet of the same width as the top white strip. The carbon paper imprint will then transfer to the lower layer, leaving a permanent imprint of either fingerprint or footprint.

Figure 4:
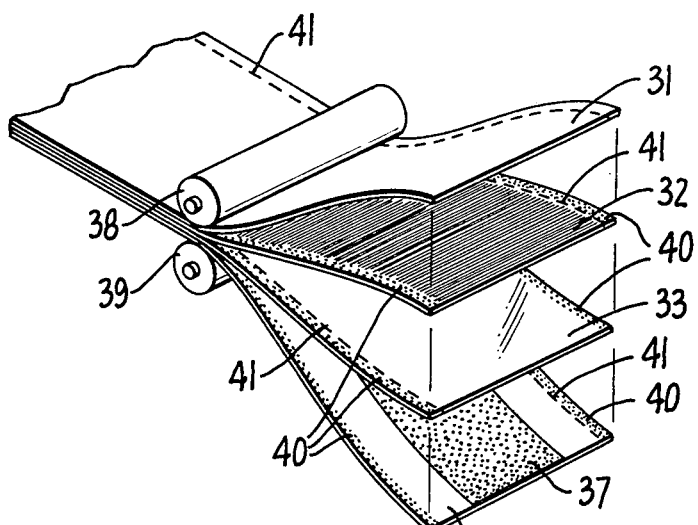
FIGS. 4, 5, 6 and 7 are each perspective views showing various assemblies and structures embodying the present invention.

Referring to FIG. 4, there is shown one embodiment of a composite test device having a multiple layer structure including a topmost or cover sheet 31, a carbon paper insert 32, a silicone coated paper sheet 33 and the bottom sheet 36 having adhesive 37 applied along the length of the strip centrally thereof. The strips are secured at their margins by adhesive 40 and assembled by passage between upper and lower rollers 38 and 39. The various sheets may also have perforations 41 along their margins as shown to facilitate removal of the silicone coated sheet from the multiple layer structure.

In use, one wishing to use the structure to test a suspected offender will grasp the righthand side of the assembled structure along the righthand side, thus releasing the joint provided upon that side of the structure. This will enable the silicone coated paper to be removed. The silicone coated paper prevents transfer from the carbon paper to the base sheet prior to use. After the structure has been used, the opposite side of the sheet is released and the record will appear upon the adhesive treadway 37.

Figure 5:
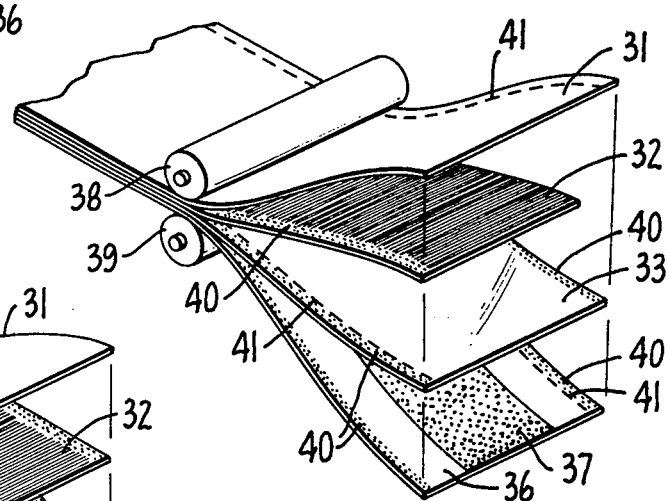

The structure shown in FIG. 5 is much like that shown in FIG. 4, except that the carbon paper does not extend completely across the silicone coated sheet.

Figure 6:
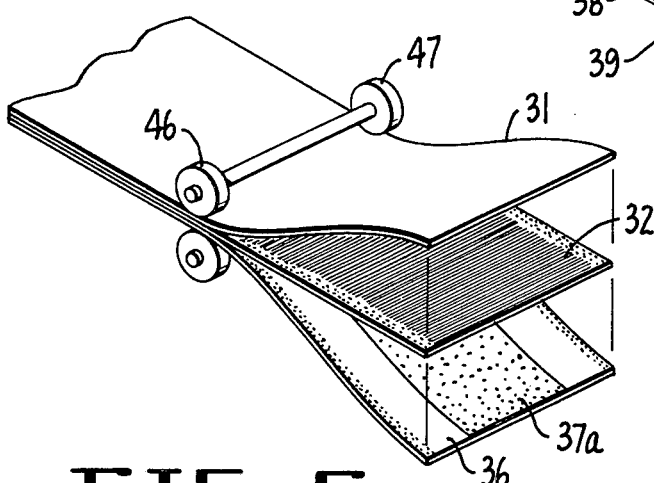

The structure shown in FIG. 6 is like that in FIGS. 4 and 5, except that the silicone coated sheet is not included. However, the pressure rollers comprise only opposite rollers 46 and 47 so that the pressure is applied only on the side edges. The adhesive treadway is provided with a light tack adhesive 37a so that the silicone coated paper is not needed.

Figure 7:
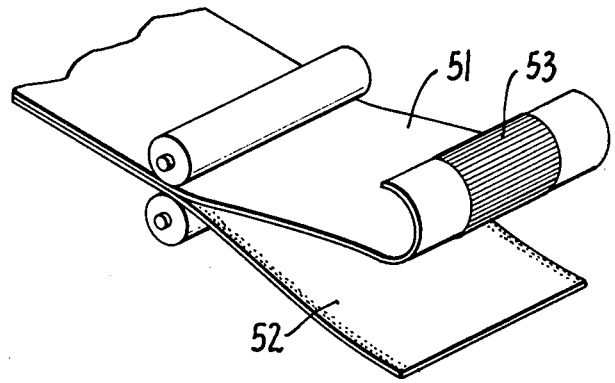

In the structure shown in FIG. 7, the top and bottom sheets 51 and 52 are provided. The underside of sheet 51 has a non-drying ink provided as a strip 53 down the length of the upper sheet 51 so that when the structure is disassembled, the record appears upon the lowermost sheet 52.

Figure 8:
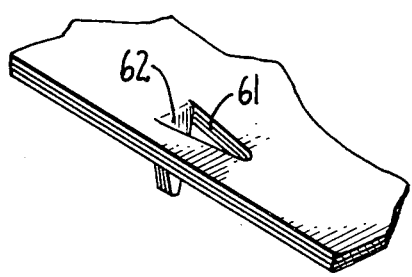
FIG. 8 is a fragmentary perspective view showing one method of procuring several sheets together.
Figure 18:
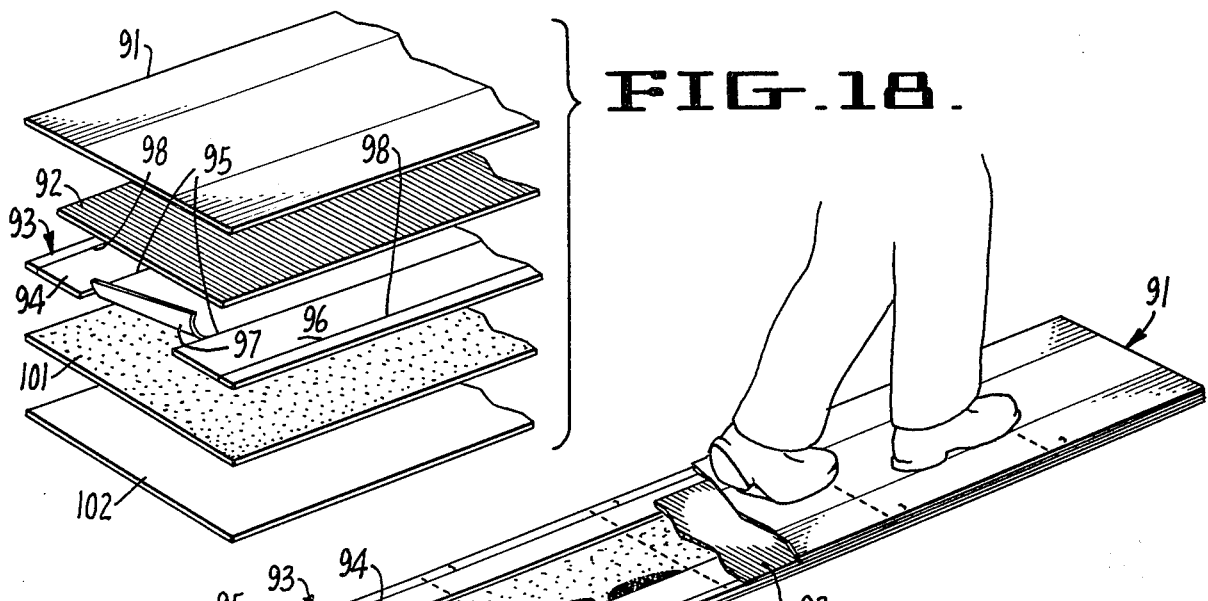
FIG. 18 is a perspective view in exploded form showing still another form of the device, several elements of the device being separated one from the other for illustrative purposes.
Figure 19:
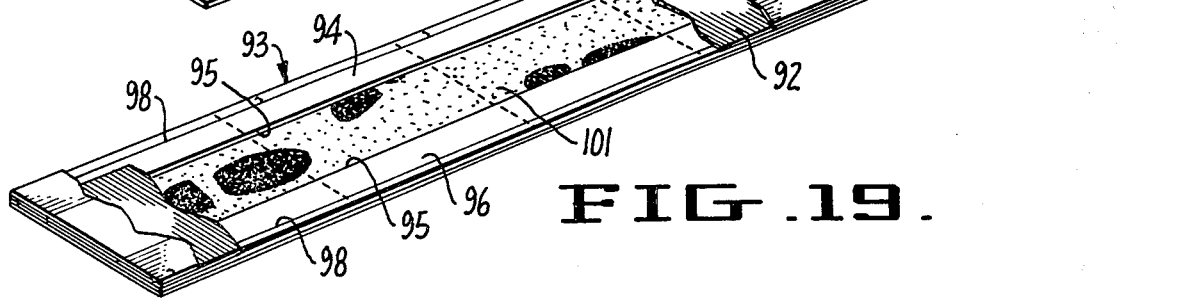
FIG. 19 shows the device of FIG. 18 in use.
Figure 20:
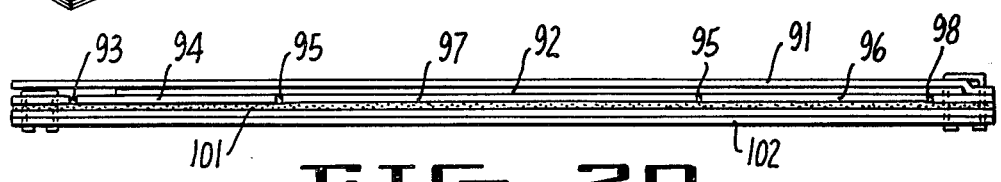
FIG. 20 is an end view of the device in assembled form.
Figure 21:
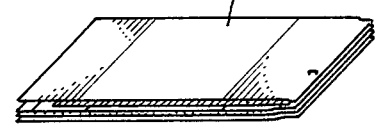
FIGS. 21 through 26 show different manipulative steps in the preparation of the device for use in recording footprints and, following such use, reassembled.
Figure 22:
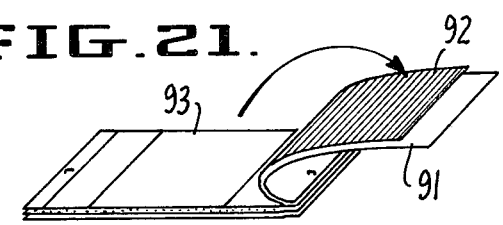
Figure 23:
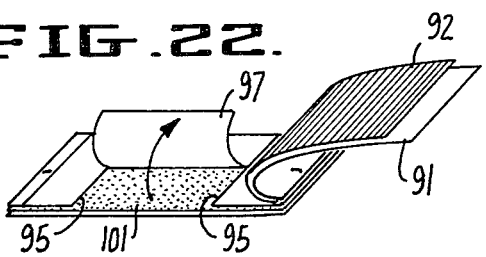
Figure 24:
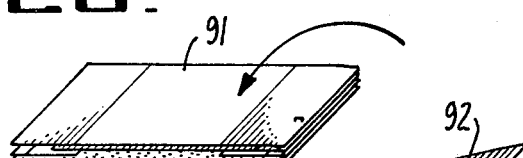
Figure 25:
Figure 26:
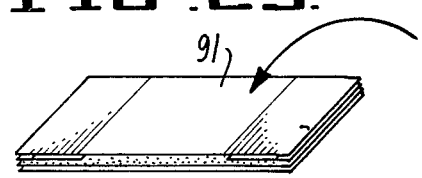

The sheets can be secured together as is shown in FIG. 8 by providing perforations 61 which provide a depending tongue 62 which holds the several sheets together at spaced intervals.

Figure 1:
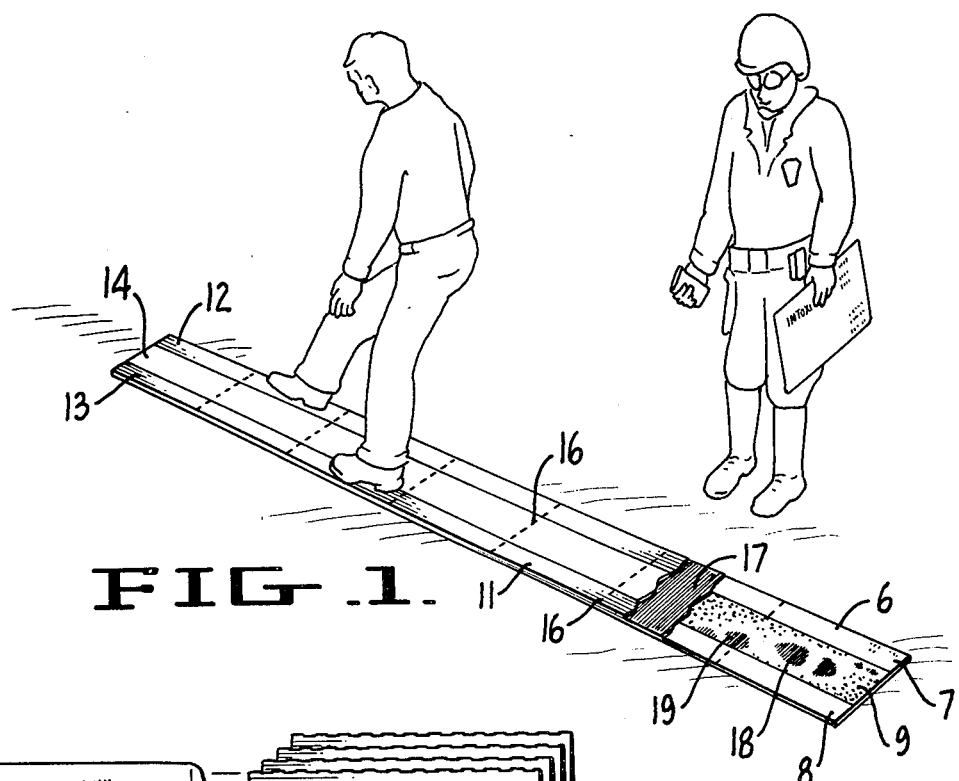
FIG. 1 is a perspective view showing a suspect undergoing a test employing the device of the present invention.
Figure 2:
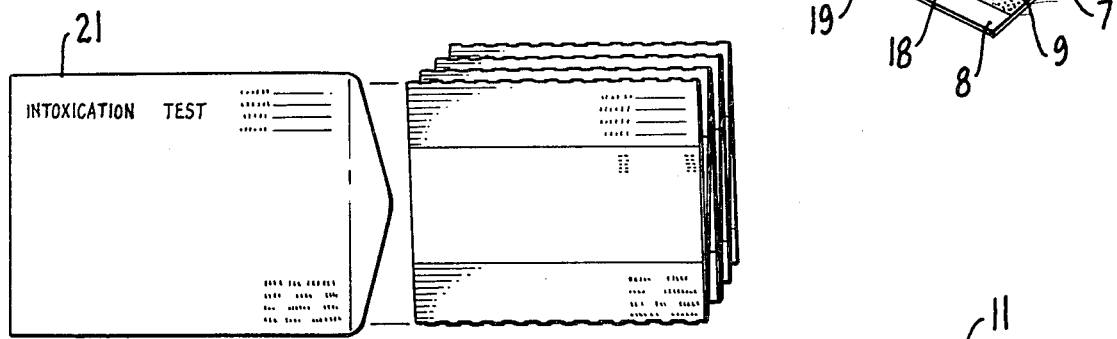
FIG. 2 is a perspective view of the test device in folded form.

In use, the several connected strips are stretched out longitudinally as appears in FIG. 1 and a person undergoing the test is asked to walk heel to toe from one end of the strip to the other. If a person falters during the test or places his foot other than in the white portion, this will be clearly indicated on the bottom sheet 9. Thus, as appears in FIG. 1, the suspect's first footprint indicated at 18 is clearly in the white portion but the next footprint 19 is to one side of the white line so that the entire print is not shown.

When the top sheet 11 is striped away and the carbon paper layer 17 removed, there is a clear record of the test given, leaving nothing to be disputed regarding the motorability of the person tested. The testing device functions equally well on asphalt, concrete or any firm surface.

The impression of prints can either be obtained by using a non-drying ink with a protective coating over the ink to prevent drying or an adhesive process so that the impression is transferred to the adhesive coated section from the carbon paper either by pressure of footprints or fingerprints on the bottom sheet. The material used to provide the top and bottom 6 and 11 are moisture resistant.

After use the assembled sheets are folded and packaged in a suitable envelope or container 21.

In the upper righthand corner of the top sheet suitable information can be entered such as the name of the testee or driver, his driver's license, the date, the location and the officer completing the test. Also, prints from each of the thumbs can be provided upon the face of the envelope or in a suitable space provided on the upper left corner of one of the lower segments of base sheet 6 and marked left and right thumb print on the device used for the heel to toe test. In the lower righthand corner, I provide instructions for use such as the following:

1. Walk from either direction.
2. Testee walks white line heel to toe. Have testee press right and left thumb in area indicated.
3. Do not separate at individual horizontal perforations.
4. Do not inspect for prints.
5. Any step on white line portion is guaranteed to transfer prints to bottom sheet.
6. Refold and return to envelope.
7. Avoid pressure to white line before and after testing to prevent undue additional prints.

Referring to FIGS. 9 through 17 and particularly to FIG. 9, the device comprises a top sheet 71 having opposite marginal side edges 72 and 73 to define two wide bands 111 and 112 on the white top sheet. Successively across the face of the upper sheet, I provide colored bands 74, 76 and 77 of a distinctive color such as blue. These colored bands are printed on the white top sheet 71 so that the colored strips 74, 76 and 77 stand out quite prominently to define the wide bands 111 and 112. On the underside of sheet 71 between the colored bands 74, 76 and 77, I provide a material which will leave a print immediately beneath the sheet 71 on sheet 81 as by bands of a carbon paper 78 and 79. Sheet 81 has colored bands corresponding to bands 74, 76 and 77. Above the bottom sheet 81 is a protective sheet 85. Bottom sheet 81 has an adhesive surface 82 thereon extending across the outer margin of the carbon paper areas 78 and 79. The several sheets are secured along one of the marginal edges by rivets or by gluing.

At opposite ends of several interconnected lengths of the described sheets, I provide adhesive strips 86 and 87 which enable one to secure the assembly in position on a flat surface such as a wood or tile floor. To prepare the unit for use, the adhesive strips 86 and 87 are affixed to the floor surface. Then the top sheet 71 is folded back, as appears in FIG. 13, on scoreline 114. Sheet 85 is then moved from its interfolded position by release from scoreline 115 to one side of the assembly (FIG. 14) along scoreline 88. The top sheet 71 is then placed over the bottom sheet 81 (FIG. 15). In this position, the carbon strips 78 and 79 are over the adhesive coated areas 82 and 83. The individual then traverses the tracks between colored strips 74, 76 and 77, as shown in FIG. 10. When traverse of the strips has been completed by the individual walking with one foot in each wide band 111 and 112, the individual's footprints will be transferred by the carbon to the adhesive surfaces 82 and 83. When this has been completed, the protective sheet 85 is then returned to position over the adhesive strips 82 and 83 upon which the transfer from the carbon strips has been completed (FIG. 17). Thus, one is provided with a complete record of the traverse of the individual's feet over the extended strips. Thus, the successive steps in the use of the device can be summarized as follows:

1. Fold back top sheet 71 on scoreline 114.
2. Lift protective sheet 85 along scoreline 88 and fold back on perforation 88 to expose adhesive strips 82 and 83.
3. Replace top sheet 71 over adhesive.
4. Remove tape liner from the adhesive strips 86 and 87 to each end of walking progress recorder and affix to smooth hard floor surface.
5. Indicate direction of patient travel with a small arrow.
6. Have the subject walk with one foot in each white track.
7. Replace protective sheet 85 and return top sheet 71 to original position. Fold strips 86 and 87 to prevent adhesive grab.
8. Place in an envelope for record purposes.

The foregoing may be repeated every three to five days to record the recovery progress of the person.

In the form of the device shown in FIGS. 18 through 26, an upper sheet 91 is provided as the uppermost sheet in the assembly. Positioned immediately beneath the upper sheet is a layer of carbon paper 92 which overlies a protective sheet 93. The opposite side portions of the sheet 93, indicated at 94 and 96, are preferably colored to leave an intermediate strip 97 of a white color. Immediately beneath sheet 93 is another sheet 101 which is coated with an adhesive and a lower cover sheet 102. The several sheets are secured along one of the longitudinal marginal edges. Sheet 93 is preferably weakened along lines 95 to permit ready removal of strip 97. In some instances, the sheet 93 is also weakened by slits 98 closely adjacent each longitudinal edge. Thus, it is possible to remove selectively the intermediate strip 97 of sheet 93 or to remove all of that portion of the protective sheet 93 between slits 98 on opposite sides of sheet 93. Thus, one is able to provide either a relatively narrow record portion of the width of the intermediate strip 97 or a wider record portion defined by the slits 98.

In use, strip 97 is removed to expose the corresponding area on lower strip 101. When the carbon paper strip 92 is in contact with strip 101, the footprints made by an individual walking the length of the sheet 91 will appear upon the lower strip 101. Upon completion of the test, the carbon paper strip 92 is removed to provide a permanent record of the tracks of the individual traversing the uppermost strip 91. The successive steps thus indicated are as follows:

1. Lift the top sheet 91, remove and discard the protective strip 97 from the center of sheet 93 to expose the adhesive strip 101 allowing the carbon to contact the adhesive.

2. The individual being tested walks heel to toe along the white line on sheet 91.

3. Any step on the white line will transfer prints to sheet 101.

4. After test, tear out carbon 92.

5. Refold test and return to its envelope.

6. If desirable, affix test device to floor or join tests together for longer track, using tape at each end of test device.

I claim:

1. A walking test device comprising an upper sheet having a central area thereon defining at least one walkway, marginal areas on either side of said at least one walkway, intermediate ink transfer means disposed only beneath the walkway on the upper sheet, a second sheet having an adhesive coated area thereon positioned below the upper sheet only in the area of said second sheet located beneath said walkway, the areas on said second sheet disposed beneath said upper sheet marginal areas being free of adhesive, said adhesive permanently receiving impressions imparted by the pressure of a walker's foot in the walkway on the upper sheet and transferred from the intermediate ink transfer surface, said areas on said second sheet which are free of adhesive not forming any impression of any portion of a walker's foot contacting said upper sheet marginal areas so that only that portion of a walker's foot which contacts said walkway will be recorded on said second sheet to thereby form a permanent record of a walker's ability to walk a straight line as such walker traverses said upper sheet during a walking test, and a removable protective sheet over said adhesive coated surface.

2. A device as in claim 1 in which the ink transfer means is provided on the underside of the upper sheet.

3. A device as in claim 1 wherein said sheets are elongate to form a track, said track having a length at least as long as a plurality of strides of a walker traversing said track.

4. A device as in claim 1 wherein the protective sheet is removable from only selected areas of the adhesive coated sheet.

5. A device as in claim 1 including a pair of central areas defining a pair of walkways each of which is positioned to be contacted by one of a walker's feet as such walker traverses said walkways.

6. The device of claim 1 further including another record area on said bottom sheet.

7. A device of claim 6 further including another test area on said cover sheet, further adhesive means coinciding with said another test area and further test area defining means on said cover sheet.

8. A device for testing a person's ability to walk in a predetermined area comprising:
a cover sheet;
a bottom sheet having at least one record area and marginal portions on either side of said record area, adhesive means on said bottom sheet only in said record area, said marginal areas being free of adhesive;
a removable intermediate sheet between said cover and bottom sheets;
at least one strip of transfer means located on the underside of said cover sheet; and
test area defining means on the marginal edges of said cover sheet defining at least one longitudinally extending test area between the marginal edges of said cover sheet for traverse by a person undergoing a test, said test area being coincident only with said bottom sheet adhesive means and said record area, said test area defining means being coincident only with said adhesive free areas of said bottom sheet, said intermediate sheet being interposed between said adhesive means and said test area for preventing transfer of markings from said cover sheet to said test area, said transfer means forming a footprint on said bottom sheet only of that portion of a person's foot which contacts said test area thereby forming a permanent record of a walker'ability to walk a straight line as such walker traverses said test area after said intermediate sheet has been removed during a walking test.

9. A test device as in claim 8 wherein the opposite marginal edges are each of a distinctive color such that the area intermediate the edge strips provides a test area to be traversed by a person undergoing a sobriety test.

10. A test device as in claim 8 in which said at least one strip of transfer means is of a carbon paper providing an imprint on the lower sheet showing the areas where the feet of the person undergoing the sobriety test were placed as the person undergoing such test walked down the length of the assembled strip.

11. A device for testing a person's ability to walk in a predetermined area comprising:
a cover sheet having a pair of longitudinally extending marginal edges;
a bottom sheet having at least one record area and marginal areas on either side of said record area, and a pair of longitudinally extending marginal edges;
adhesive means on said bottom sheet only in said at least one record area of said bottom sheet with the areas adjacent each of said bottom sheet marginal areas being free of adhesive;
a removable intermediate sheet removably secured on said bottom sheet and located between said cover and bottom sheets and covering said adhesive means;
at least one strip of transfer means located on the undersurface of said cover sheet; and
at least one test area defining means on said cover sheet adjacent the longitudinally extending marginal edges of said cover sheet, said test area defining means including a pair of strips of distinctive marking, said strips coinciding with said marginal areas and each having a width equal to the width of a corresponding adhesive free area on said bottom sheet, said strips covering only said adhesive free areas, the area on said cover sheet between said strips defining an intermediate longitudinally extending test area covering the area of said cover sheet between said strips, said cover sheet being traversed by a person undergoing a test, said test area being coincident only with said bottom sheet adhesive means and said record area, said intermediate sheet being interposed between said adhesive means and said test area for preventing transfer of markings from said cover sheet to said record area, said transfer means forming a footprint on said bottom sheet in said record area only of that portion of a person's foot which contacts said test area thereby forming a permanent record of a walker's ability to walk a straight line as such walker traverses said cover sheet after said intermediate sheet has been removed during a walking test.

12. The device of claim 11 further including another record area on said bottom sheet.

13. The device of claim 12 further including another test area on said cover sheet, further adhesive means coinciding with said another test area and further test area defining means on said cover sheet.

* * * * *